(12) United States Patent
Smous et al.

(10) Patent No.: US 7,705,980 B2
(45) Date of Patent: Apr. 27, 2010

(54) METHOD FOR CORRECTING A SPECTRAL IMAGE FOR OPTICAL ABERRATIONS USING SOFTWARE

(75) Inventors: James E. Smous, Niles, MI (US); Mihailo V. Rebec, Bristol, IN (US); Michael P. Houlne, Centennial, CO (US)

(73) Assignee: Bayer Healthcare LLC, Tarrytown, NY (US)

( * ) Notice: Subject to any disclaimer, the term of this patent is extended or adjusted under 35 U.S.C. 154(b) by 200 days.

(21) Appl. No.: 11/894,511

(22) Filed: Aug. 21, 2007

(65) Prior Publication Data

US 2008/0059100 A1    Mar. 6, 2008

Related U.S. Application Data

(60) Provisional application No. 60/839,166, filed on Aug. 22, 2006.

(51) Int. Cl.
*G01J 3/44* (2006.01)
*G01N 21/64* (2006.01)
*G01N 21/65* (2006.01)

(52) U.S. Cl. .................................... 356/301; 356/318
(58) Field of Classification Search ................ 356/301, 356/317, 318
See application file for complete search history.

(56) References Cited

U.S. PATENT DOCUMENTS

| | | | | |
|---|---|---|---|---|
| 4,634,276 A | 1/1987 | Sharpe | ....................... | 356/305 |
| 4,645,340 A | 2/1987 | Graham et al. | ............... | 356/301 |
| 5,560,356 A | 10/1996 | Peyman | ....................... | 128/633 |
| 5,615,673 A | 4/1997 | Berger et al. | ................ | 128/633 |
| 5,754,289 A | 5/1998 | Ozaki et al. | .................. | 356/301 |
| 5,923,482 A | 7/1999 | Gilby | ......................... | 359/846 |
| 6,044,285 A | 3/2000 | Chaiken et al. | ............. | 600/316 |
| 6,070,093 A | 5/2000 | Oosta et al. | .................. | 600/316 |
| 6,137,641 A | 10/2000 | Gilby | ......................... | 359/846 |
| 6,167,290 A | 12/2000 | Yang et al. | ................... | 600/322 |

(Continued)

FOREIGN PATENT DOCUMENTS

| | | |
|---|---|---|
| EP | 0 129 289 B1 | 9/1990 |
| EP | 0 636 232 B1 | 1/1998 |
| WO | WO 03/011764 A3 | 2/2003 |
| WO | WO 03/023339 A1 | 3/2003 |
| WO | WO 03/056311 A1 | 7/2003 |
| WO | WO 2004/023125 A2 | 3/2004 |
| WO | WO 2004/064627 A1 | 8/2004 |
| WO | WO 2006/127766 A1 | 11/2006 |

OTHER PUBLICATIONS

Berger et al., "Feasibility of Measuring Blood Glucose Concentration by Near-Infrared Raman Spectroscopy," Spectrochimica Acta. Part A: Molecular Spectroscopy, Pergamon Press, Oxford, GB, vol. 53A, No. 2, dated Feb. 1997, pp. 287-292.

(Continued)

*Primary Examiner*—F. L Evans
(74) *Attorney, Agent, or Firm*—Nixon Peabody LLP

(57) ABSTRACT

A spectral image is corrected for optical aberrations. Tissue is exposed to a high-intensity, narrow band of light. The narrow band of light is scattered by at least one analyte in the tissue. Raman signals are optically collected from the scattered light. The Raman signals are directed to a wavelength-separating device. The Raman signals are detected as a function of intensity and wavelength to create the spectral image. The spectral image is corrected for optical aberrations using a software algorithm to spatially reassign intensity. The software may be adapted to use a reference image to make dynamic corrections. Fluorescence signals may also be collected.

19 Claims, 6 Drawing Sheets

U.S. PATENT DOCUMENTS

| | | | |
|---|---|---|---|
| 6,223,063 B1 | 4/2001 | Chaiken et al. | 600/310 |
| 6,289,230 B1 | 9/2001 | Chaiken et al. | 600/322 |
| 6,292,686 B1 | 9/2001 | Chaiken et al. | 600/476 |
| 6,332,092 B1 | 12/2001 | Deckert et al. | 600/476 |
| 6,352,502 B1 | 3/2002 | Chaiken et al. | 600/4.73 |
| 6,377,828 B1 | 4/2002 | Chaiken et al. | 600/316 |
| 6,389,306 B1 | 5/2002 | Chaiken et al. | 600/474 |
| 6,486,948 B1 | 11/2002 | Zeng | 356/301 |
| 6,503,478 B2 | 1/2003 | Chaiken et al. | 429/9.1 |
| 6,560,478 B1 | 5/2003 | Alfano et al. | 600/473 |
| 6,574,490 B2 | 6/2003 | Abbink et al. | 600/316 |
| 6,615,061 B1 | 9/2003 | Khalil et al. | 600/310 |
| 6,636,305 B2 | 10/2003 | Zhao et al. | 356/301 |
| 6,681,133 B2 | 1/2004 | Chaiken et al. | 600/473 |
| 6,690,966 B1 | 2/2004 | Rava et al. | 600/473 |
| 7,226,166 B2 * | 6/2007 | Della Vecchia et al. | 351/221 |
| 7,308,293 B2 | 12/2007 | Gerlitz | 600/318 |
| 2003/0023170 A1 | 1/2003 | Gardner et al. | 600/476 |
| 2003/0071993 A1 | 4/2003 | Zhao et al. | 356/300 |
| 2003/0120137 A1 | 6/2003 | Pawluczyk | 600/310 |
| 2004/0152992 A1 | 8/2004 | Zeng | 600/476 |
| 2004/0257529 A1 | 12/2004 | Thomas | 351/205 |
| 2005/0043597 A1 | 2/2005 | Xie | 600/315 |
| 2006/0001870 A1 | 1/2006 | Voigt et al. | 356/301 |
| 2008/0051645 A1 | 2/2008 | Rebec et al. | 600/316 |

OTHER PUBLICATIONS

Written Opinion corresponding to International Patent Application Serial No. PCT/US2007/018234, European Patent Office, dated Mar. 10, 2008, 7 pages.

International Search Report corresponding to International Patent Application Serial No. PCT/US2007/018234, European Patent Office, dated Mar. 10, 2008, 4 pages.

Z. Huang, H. Zeng, I. Hamzavi, D. McLean, and H. Lui, "Rapid Near-Infrared Raman Spectroscopy System for Real-Time In Vivo Skin Measurements", Optics Letters, 26 (22), 1782-1784 (2001).

"A Noninvasive Glucose Monitor: Preliminary Results in Rabbits" by Mark S. Borchert, M.D., et al., *Diabetes Technology & Therapeutics*, vol. 1, No. 2, 1999, Mary Ann Liebert, Inc. (pp. 145-151).

"Laser-Based Measurement of Glucose in the Ocular Aqueous Humor: An Efficacious Portal for Determination of Serum Glucose Levels" by Paul G. Steffes, Ph.D., *Diabetes Technology & Therapeutics*, vol. 1, No. 2, 1999, Mary Ann Liebert, Inc. (pp. 129-133).

* cited by examiner

US 7,705,980 B2

METHOD FOR CORRECTING A SPECTRAL IMAGE FOR OPTICAL ABERRATIONS USING SOFTWARE

CROSS-REFERENCE TO RELATED APPLICATION

This application claims priority to U.S. Provisional Application Ser. No. 60/839,166 filed on Aug. 22, 2006 which is incorporated by reference in its entirety.

FIELD OF THE INVENTION

The present invention generally relates to a method of correcting a spectral image using software. The method may be used to assist in determining an analyte concentration.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, it is important that diabetic individuals frequently check the glucose level in their body fluids to regulate the glucose intake in their diets. The results of such tests can be used to determine what, if any, insulin or other medication needs to be administered.

In some existing techniques, a lancet may be used to draw fluid (e.g., blood) from a user. This fluid is then used with an instrument or meter to determine an analyte concentration. It would be desirable to eliminate the need to use a lancet, while still accurately determining the analyte concentration. Such applications are referred to as non-invasive techniques.

One non-invasive technique involves using Raman signals to determine the concentration of an analyte such as glucose. There, however, are disadvantages in existing non-invasive methods that use Raman or other types of signals. For example, the spectral image of an object that is imaged using a spectrometer contains optical aberrations. Optical aberrations such as curvature may result in overlapping spectral bands and/or poorly resolved peaks. This may lead to erroneous results when attempting to quantify an analyte in a complex matrix. These optical aberrations may make it difficult to distinguish or differentiate analytes (e.g., glucose) from other tissue and fluid components with similar characteristic spectra. Some existing techniques have proposed hardware solutions to correct the optical aberrations. These hardware solutions, however, do not have the flexibility to address selected optical aberrations. For example, existing hardware techniques are not adapted to address curvatures that are not fixed such as those associated with holographic or transmission grating.

It would be desirable to have a method that has flexibility in addressing a variety of optical aberrations in spectral images.

SUMMARY OF THE INVENTION

According to one method, a spectral image is corrected for optical aberrations. Skin tissue or other tissue is exposed to a high-intensity, narrow band of light. The narrow band of light is scattered by at least one analyte in the skin tissue or other tissue. Raman signals are optically collected from the scattered light. The Raman signals are directed to a wavelength-separating device. The Raman signals are detected as a function of intensity and wavelength to create the spectral image. The spectral image is corrected for optical aberrations using a software algorithm to spatially reassign intensity.

According to another method, the concentration of at least one analyte in a fluid is determined. Skin tissue or other tissue is exposed to a high-intensity, narrow band of light. The narrow band of light is scattered by at least one analyte in the skin tissue or other tissue. Raman signals are optically collected from the scattered light. The Raman signals are directed to a wavelength-separating device. The Raman signals are detected as a function of intensity and wavelength to create the spectral image. The spectral image is corrected for optical aberrations using a software algorithm to spatially reassign intensity. The concentration of the at least one analyte is determined using the corrected spectral image.

According to a further method, a spectral image for optical aberrations is corrected using an instrument. Skin tissue or other tissue is exposed to a high-intensity band of light. An image of the skin tissue or other tissue is optically collected. The image is dynamically corrected using software to optically correct for at least one of the instrument and skin tissue or other tissue. Information from the corrected image is used to perform a general diagnosis.

According to yet another method, a spectral image for optical aberrations is corrected using an instrument. Skin tissue or other tissue is exposed to a high-intensity light. The light is scattering by at least one analyte in the skin tissue or other tissue. Fluorescence signals are optically collected from the scattered light. The fluorescence signals are directed to a wavelength-separating device. The fluorescence signals are detected as a function of intensity and wavelength to create the spectral image. The spectral image are collected for optical aberrations using a software algorithm to spatially reassign intensity.

In another method, a spectral image is corrected for optical aberrations. Raman signals from the scattered light are optically collected. The Raman signals are directed to a wavelength-separating device. The Raman signals are detected as a function of intensity and wavelength to create the spectral image. The spectral image is corrected for optical aberrations using a software algorithm to spatially reassign intensity.

In yet another method, a spectral image is corrected for optical aberrations using an instrument. Fluorescence signals from the scattered light are optically collected. The fluorescence signals are directed to a wavelength-separating device. The fluorescence signals are directed as a function of intensity and wavelength to create the spectral image. The spectral image is corrected for optical aberrations using a software algorithm to spatially reassign intensity.

BRIEF DESCRIPTION OF THE DRAWINGS

The foregoing and other advantages of the invention will become apparent upon reading the following detailed description and upon reference to the drawings.

FIG. 2b depicts a detector with a corrected spectral image of FIG. 2a.

FIG. 3a is representative spectra generated from an uncorrected spectral image of a type of aberration depicted in FIG. 2a.

FIG. 3b is the representative spectra generated from a corrected spectral image of FIG. 3a.

DETAILED DESCRIPTION OF ILLUSTRATED EMBODIMENTS

Figure 1:
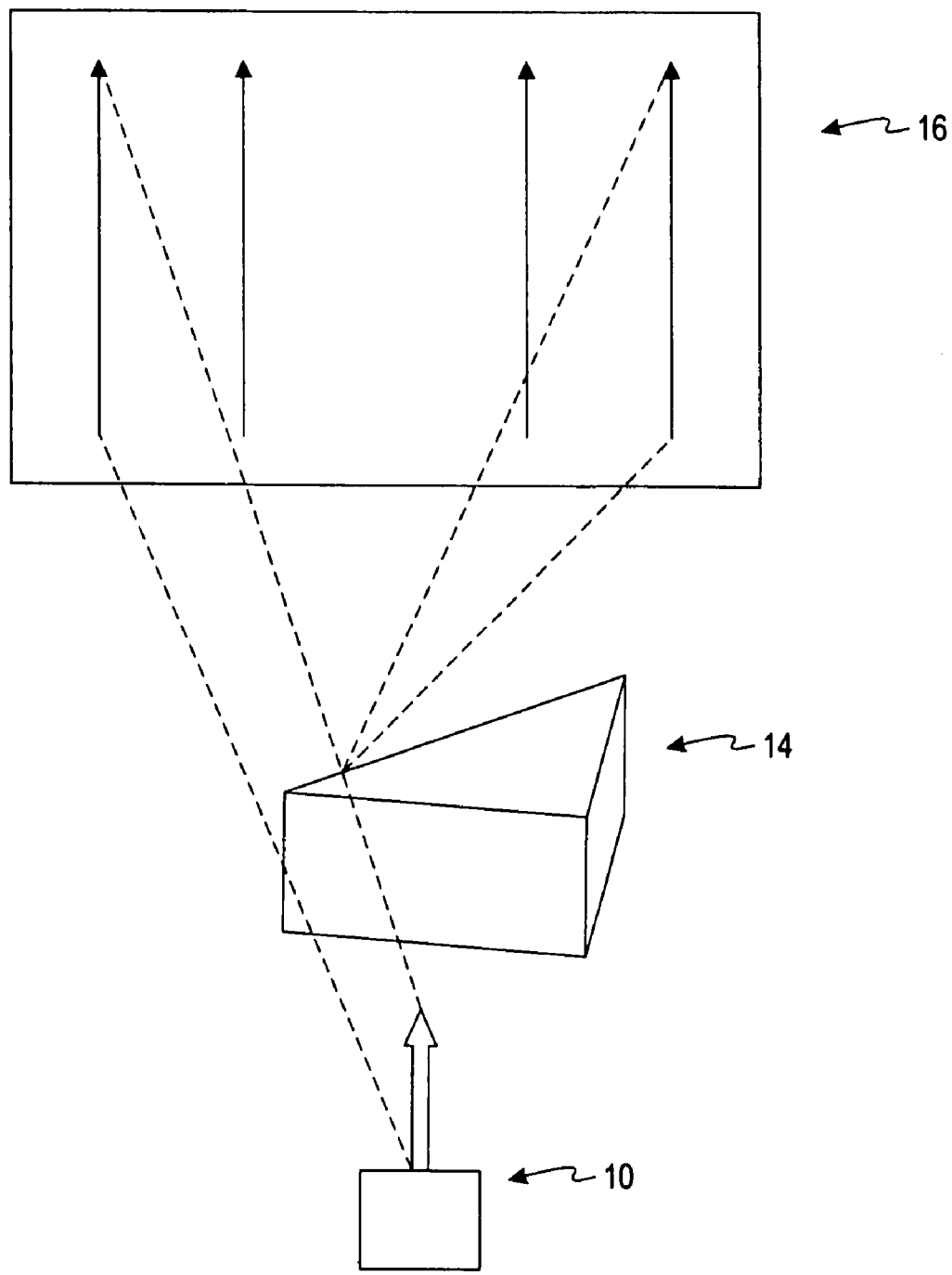
FIG. 1 depicts a sequence of acts in producing a corrected spectral image according to one method.

The present invention is directed to a software method for correcting optical aberrations of a spectral image in a wavelength-separating device. By reducing or eliminating the optical aberrations, in one method, a quantitative analysis of an analyte can be determined in a non-invasive manner. It is highly desirable for the software method to preserve spectral resolution in quantifying a particular analyte.

Analytes that may be measured include glucose, lipid profiles (e.g., cholesterol, triglycerides, LDL and HDL), microalbumin, fructose, lactate, bilirubin, creatinine, uric acid, potassium, sodium, chlorine, and pH. It is contemplated that other analyte concentrations may be determined. As used within this application, the term "concentration" refers to an analyte concentration, activity (e.g., enzymes and electrolytes), titers (e.g., antibodies), or any other measure used to determine the desired analyte.

To determine the analyte concentration in a quantitative, non-invasive manner, the optical images in one method are summed vertically to generate a spectrum. The ability to distinguish analytes (e.g., glucose) from other tissue and fluid components relies on the ability to differentiate the characteristic spectra of the analyte of interest.

According to one method, a spectral image is corrected for optical aberrations by exposing skin tissue or other tissue to a narrow band of light. The narrow band of light is scattered by at least one analyte in the skin tissue or other tissue. In this method, the Raman light from the scattered light is optically collected. The Raman light is directed to a wavelength-separating device. The Raman light is detected as a function of intensity and wavelength to create the spectral image. The spectral image is corrected for optical aberrations using a software algorithm to spatially reassign intensity or, in other words, to reassign intensity values in wavelength space.

In one method, the high-intensity, narrow-band light source may come from a variety of sources. For example, the high-intensity, narrow-band light source may come from a monochromatic light source that is delivered in a narrow band. One example of a monochromatic light source is a laser-diode source. It is contemplated that other light sources may be used such as a light-emitting diode and incoherent lamps. The light sources may be filtered to provide a more clearly defined (i.e., narrow) band of light. It is also contemplated that the high-intensity, narrow-band light may be a dye laser, gas laser, ion laser or a pumped laser.

In one embodiment, a polychromatic light source is combined with appropriate filtering to yield a narrow band of light. Using such appropriate filtering, the obtained narrow band of light may be similar to monochromatic light. It is contemplated that an incoherent light source such as a light-emitting diode (LED) or a light bulb may yield a narrow band of light. In Raman applications, the LEDs or light bulb would desirably use filtering. It is contemplated that in other non-Raman applications that use LEDs or light bulbs may not need filtering. It is contemplated that other monochromatic or polychromatic sources of light may be used to obtain a narrow band of light.

The wavelength of the light source may vary but is generally from about 300 to about 10,000 nm. The light source may be an ultraviolet light source, a near-infrared light source, an infrared light source, or visible light source with appropriate filtering. The light source to be used would be a high-intensity, narrow band of light.

The Raman spectral information in one method may be collected in the wavelength range from about 300 nm to about 12,000 nm. However, several wavelength-dependent characteristics unique to tissue optics and to the Raman effect can significantly impact the ability to successfully employ the Raman technique for the non-invasive determination of analytes in tissue. For example, at lower wavelengths, the inherent Raman signal from analytes in tissue is relatively strong, but tissue autofluorescence is also relatively strong, which may overwhelm and complicate detecting the Raman signal in the tissue. Conversely, at higher wavelengths, tissue autofluorescence and the inherent Raman signal decrease. The choice of the light source would be made based on a balance of the Raman signal power and the autofluorescence interference at the wavelengths of interest for the analyte of interest. Therefore, for glucose analysis, it is desirable to employ a high-intensity, narrow band light source centered at or near 830 nm and collect the Raman spectral information in the wavelength range of from above 800 nm to about 1050 nm where the strength of the Raman signal is optimized verses the tissue autofluorescence.

The glucose-related Raman spectral information may be collected from Raman scattered light shifted from 100 $cm^{-1}$ to 10,000 $cm^{-1}$ away from the light source. More specifically, the glucose-related Raman spectral information may be collected from Raman scattered light shifted from 100 $cm^{-1}$ to 1600 $cm^{-1}$ away from the light source since the strongest glucose peaks occur at Raman shifts of about 1340 $cm^{-1}$ and about 1125 $cm^{-1}$. It is contemplated that the Raman spectral information may be collected in different ranges, especially if the analyte concentration to be determined is not glucose.

One specific example is an 830 nm laser-diode source. One example of a commercially available 830 nm laser-diode source is Invictus™ NIR 830 nm diode laser, which is marketed by Kaiser Optical Systems, Inc. of Ann Arbor, Mich. Another example is a PI-ECL-830-300 diode laser, which is marketed by Process Instruments of Salt Lake City, Utah. In one embodiment, the laser light is delivered to the skin tissue or other tissue in about a 1 mm beam diameter. It is contemplated that other laser-diode sources may be employed.

The high-intensity, narrow band of light may be adjusted so that a higher resolution Raman spectrum is generated. For example, the high-intensity narrow band of light may be limited, resulting in less light being exposed and a higher resolution Raman signal being obtained. By adjusting the high-intensity, narrow band of light, the strength of the Raman signal and the exposure may be optimized depending on the analyte of interest.

It is contemplated that different wavelength-separating devices may be used in the present invention. Wavelength-separating devices that may be used in the inventive methods include defraction elements and filters. Defraction elements generally break up the light into individual components. Filters spatially separate groups of wavelengths. Some filters selectively allow a desired group of wavelengths to pass therethrough, while preventing or inhibiting undesirable wavelengths from passing therethrough. Other filters selectively reflect a desired group of wavelengths, while allowing undesirable wavelengths to pass therethrough. The resultant image from a filtering embodiment is a select group of wavelengths.

Examples of defraction elements that may be used include, but are not limited to, holographic gratings, diffraction gratings, optical crystals and prisms. Holographic gratings and diffraction grating use plane-grating techniques to form its spectral images. Examples of filters that may be used include, but are not limited to, acousto-optical tunable filters (AOTF) and liquid crystal tunable filters (LCTF).

The detector may be a multi-pixel detector. Examples of multi-pixel detectors include, but are not limited to, a charge-coupled device (CCD), a diode array or films. It is contemplated that other multi-pixel detectors may be used. A CCD takes the received light and displays it as a function of intensity and wavelength. One example of a CCD includes a pixel array of 1300 rows of pixels in the vertical direction and 1340 columns of pixels in the horizontal direction. It is contemplated that the CCD may have a different number of rows in the vertical direction or columns in the horizontal direction. It is contemplated that the detector may be a movable single-pixel detector. For example, a single-pixel detector with a movable slit may be used. In another embodiment, the detector may be a diode array.

The software includes an algorithm that re-maps pixel values in an aberrant optical image to match the pixel values of a correct image of the object. In other words, the algorithm after being implemented properly displays the original image. The algorithm selects how the aberrant pixels are to be re-mapped by comparing the aberrant image to an image with a non-aberrated image. An undesired aberration occurs when lights interacts with optical elements (e.g., lens, gratings, filters, detector, etc.). By using a software algorithm to correct for optical aberrations, the inventive method improves operational flexibility. For example, if a lens is changed in the wavelength-separating device causing a known aberration, the software algorithm could be programmed to correct for this new aberration. The software algorithm may also assist in addressing small changes in optical alignment.

In one specific application, a spectral image may be formed using a vertical straight slit image. The intensity of the spectral image in this embodiment is typically determined by vertical binning. For chemical identification and quantitative analysis, the slit image is summed vertically to form the spectrum. The image of a straight, vertical slit through a holographic wavelength separating device, for example, results in a curved image because light rays from different positions along the length of the vertical slit are incident on the grating at different, oblique angles. An uncorrected spectral image using a vertical straight slit image includes curvature. That curvature results in a poorly resolved spectrum with significant spectral band broadening and the loss of resolution after binding. Thus, the optical aberration to be corrected in this embodiment is the curvature associated with the method of using a vertical straight slit image.

In another method, the spectral image to be corrected by software may include the use of an AOTF. When using an AOTF, the system can operate in a number of modalities. One modality includes individual wavelength or narrow wavelength regions being passed through the filter and collected by a detector (e.g., a CCD). The aberrations inherent in the AOTF and collection optics create a poorly resolved image, especially when added together or integrated. The software correction process is used to reconstruct a sharply resolved image. The software-correction process may correct for two-dimensional aberrations as well as intensity aberrations. The second modality is the collection of multiple single wavelength images. Those individual wavelength images are combined together to form a spectral image. This spectral image may be offset by a certain degree. By using a software algorithm to correct the spectral image, the spectral image may be realigned to prevent or reduce blurring in the image. In such a method, the horizontal and vertical portions of the spectral image may be corrected. Some optical aberrations that may be addressed by the software include positioning changes, non-coherent fibers, lens aberrations, crystal inconsistencies, intensity aberrations, and collection-efficacy variations.

In one method, the light (e.g., Raman signals) is collected and detected using a spectrometer. The spectrometer is a device that collects and separates the light. The spectrometer includes collection optic(s), a wavelength-separating device and a detector. The spectrometer may also include a light source. The collection optic(s) assists in collecting and directing the light (e.g., Raman light) through the wavelength-separating device. The wavelength-separating device separates the light into separate wavelength components. The detector detects the light as a function of intensity and wavelength to create the spectral image. The spectrometer may further include focusing optic(s) that assists in directing and focusing the Raman light exiting from the wavelength-separating device onto the detector.

Referring to FIG. 1, an object 10 is shown being imaged through a wavelength-separating device 14, which is a prism in this embodiment. The Raman light is detected as a function of intensity and wavelength to create the spectral image by a detector 16. The detector in this embodiment is a charge-coupled device (CCD). The spectral image depicted in the detector 16 of FIG. 1 is a desired corrected spectral image.

As discussed above, one uncorrected aberration of a spectral image may be characterized by curvature of an image. The curvature of an image occurs when the image is passed through a wavelength-dispensing device. One example of an uncorrected image with curvature is shown on a detector in FIG. 2a. The uncorrected image of FIG. 2a may be from a plane-grating spectrometer that uses generally straight vertical slits.

Figure 2A:
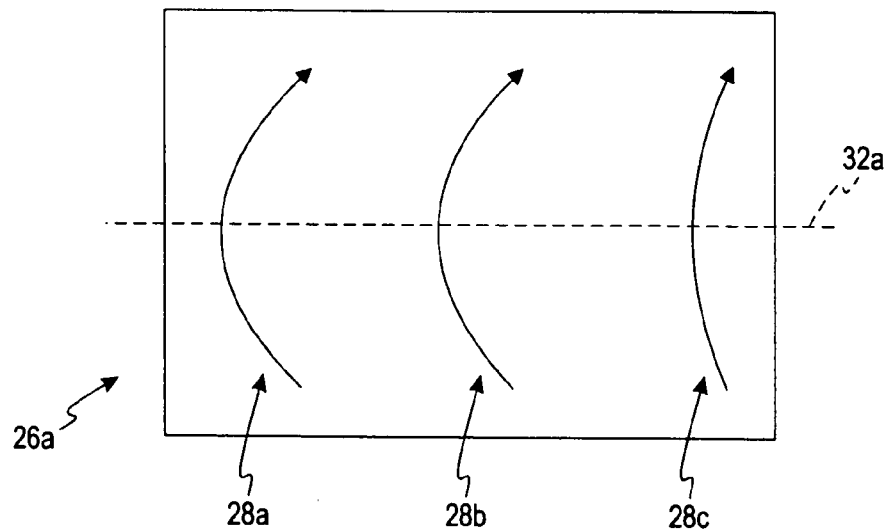
FIG. 2a depicts a detector with an uncorrected spectral image according to one embodiment.
Figure 2B:
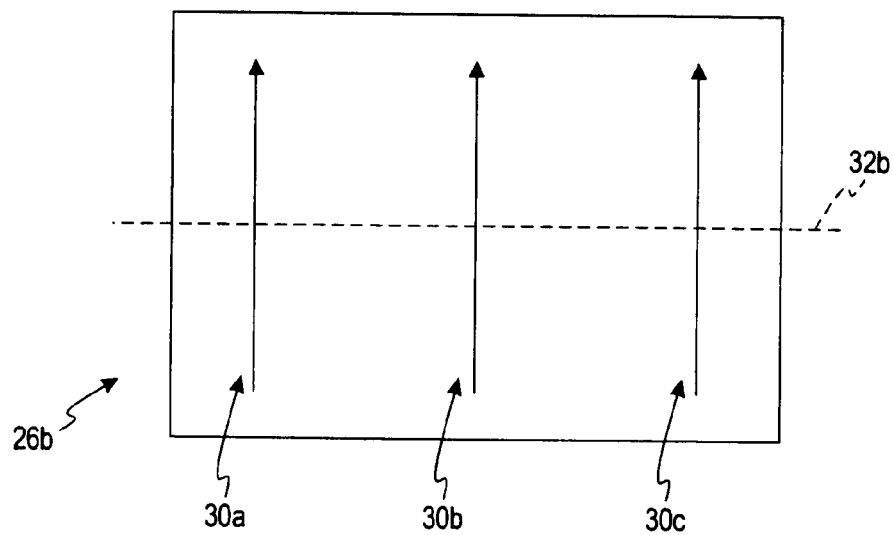

Specifically, FIG. 2a depicts a detector 26a with a plurality of curved line images 28a-c of the vertical slits. FIG. 2a depicts a spectral image that has not been corrected by a software algorithm. FIG. 2b depicts a detector 26b with a plurality of corrected line images 30a-c that are generally straight vertical lines. The corrected line images 30a-c of FIG. 2b were corrected using a curvature-correction software algorithm. The horizontal axis of the detectors 26a,b depicts the wavelength components of the Raman light, while the vertical axis depicts the measure of the vertical slit height. The wavelength increases going from left to right on the horizontal axis of FIG. 2b. The intensity of the light corresponds to the quantity of the wavelength component of the Raman light.

In one method to correct curvature, the software algorithm begins by using a vertical center (shown as dashed lines 32a, 32b in respective FIGS. 2a, 2b) of the curve as a reference point. The curvature-correction algorithm shifts intensity values in pixels above and below the dashed line 32a shown in FIG. 2a. By shifting the intensity values in the pixels, the shifted pixels will be aligned with the reference pixels as shown in, for example, FIG. 2b.

Figure 3A:
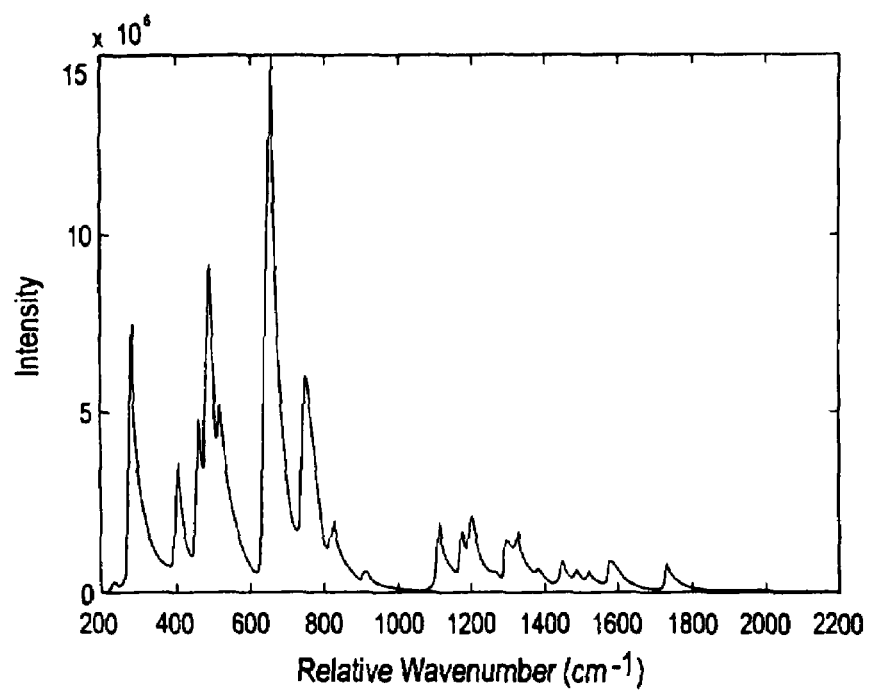
Figure 3B:
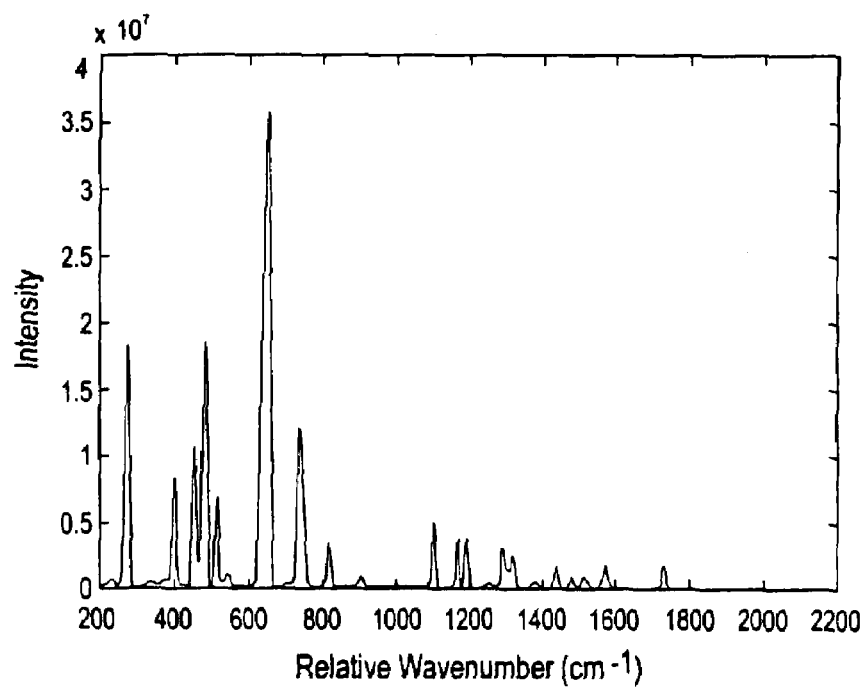

FIG. 3a shows a representative spectrum of a neon light source constructed from a curved line, while FIG. 3b shows a spectrum of the neon light source reconstructed from the corrected line image. The spectrums of FIGS. 3a, 3b were generated from the respective uncorrected and corrected images by vertically summing the pixel values. The peak shapes in the uncorrected spectrum (FIG. 3a) showed significant tailing on the right side of the image and overlapping adjacent peaks. Thus, the spectral resolution of FIG. 3a was degraded. Such a degraded image may destroy valuable information pertaining to chemical structure and identification. FIG. 3b, on the other hand, showed peaks in the spectrum that were highly resolvable and, therefore, more characteristic of neon. The corrected spectral resolution of FIG. 3b showed less degradation, if any, as compared to the uncorrected spectral resolution of FIG. 3a.

Figure 4:
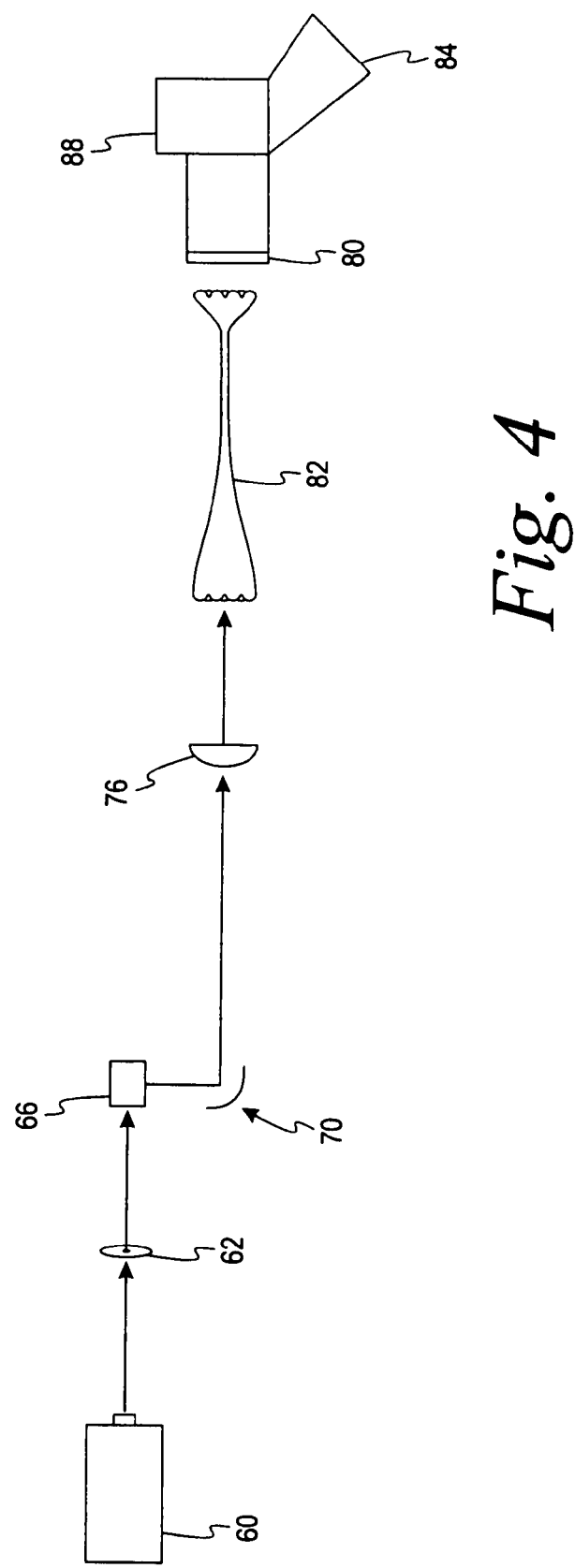
FIG. 4 is a sequence of apparatus that assists in creating a spectral image that is corrected by software for optical aberrations according to one process.

Referring to FIG. 4, a sequence of apparatus is shown that assists in creating a spectral image that is corrected by software for optical aberrations according to one process. FIG. 4 includes a laser source 60 that generates a narrow band of light. The laser light is transmitted through a lens 62 onto skin tissue 66. The narrow band of light is scattered by at least one analyte in the skin tissue. A collection mirror 70 assists in collecting the scattered light from the skin tissue 66. It is contemplated that other mirrors may be used in collecting the scattered light such as a parabolic mirror. The collected light is directed to a wavelength-separating device such as an acousto-optical tunable filter (AOTF) 76. The collected light is directed to at least one slit 80 via a fiber bundle 82. In one embodiment, the fiber bundle may form the slit. The fiber bundle 82 assists in directing the collected light into the at least one slit 80. The fiber bundle is one example of additional detector-focusing optics that assist in directing and focusing the light from the wavelength-separating device onto the detector. It is contemplated that other detector-focusing optics may be used to assist in directing and focusing the light from the wavelength-separating device onto the detector. The light is detected by a detector as a function of intensity and wavelength to create the spectral image. One example of a detector is shown in FIG. 4 as a CCD 84 with grating 88. The spectral image is corrected for optical aberrations using a software algorithm to spatially reassign intensity.

The optical aberrations may be corrected using different algorithms. In one method, to correct the curvature that is seen when using a holographic grating, a neon-calibration lamp is used to create a "feature rich" spectrum on a CCD array. The calibration lamp typically covers the spectral range of interest and is imaged across the entire area of the CCD. In one example, the spectral lines from the neon source appear as a set of curved lines imaged on the CCD such as shown in FIG. 2a. The degree of curvature, however, is not necessarily the same across the face of the CCD.

The image that is formed on the CCD may be broken up into many different spectra by reading out each row of the CCD. Each of these spectra looks generally similar in structure, but the data may appear to be stretched or shifted due to the curvature of the spectral lines. To correct this curvature, original data of these individual spectra may be shifted to eliminate the curvature in FIG. 2a.

For example, if a 1340 column by 1300 row pixel CCD were to be used, the image may be divided into 26 horizontal spectra. Each of the 26 horizontal spectra is created by summing or binning 50 adjacent vertical pixels so as to create a 1340×26 array. The vertical binning is done to smooth the data vertically. The number of binned pixels may be adjusted to minimize local curvature effects. A reference spectrum is selected that lies in the vertical center of the array (see, e.g., dashed line 32a in FIG. 2a). Typically, the reference spectrum is positioned on the curvature apex. This reference spectrum is not modified, but the uncorrected spectra that is located above and below the reference spectrum is stretched and shifted to match the relative shape of the reference spectrum.

To stretch the spectra, a small section on each end of the reference spectrum (see, e.g., FIG. 5 with apex pixel locations 120 and 140) is chosen as the model spectra. The location of these model spectra is recorded. A search routine is then called to locate the left and right model spectra in all of the uncorrected spectra above and below the reference spectrum as shown in FIG. 6. The locations of the left and right model spectra is recorded. From this data, how many pixels at each end of the uncorrected spectrum would need to be shifted to be realigned with the reference spectrum is determined.

In one method, to determine the amount of pixel shift at each pixel location within one uncorrected spectrum, a linear equation is formed from the two offset values for that spectrum, and a pixel offset value is then calculated for all pixel locations within that spectrum. This calculation results in 26 linear equations, one for each row of the binned spectra. Using these equations, a second 1340×26 shift map is created by calculating the pixel shift values for each pixel in the binned array. To map the pixel shift values of the entire 1340×1300 array, pixel shift values are interpolated and extrapolated vertically from the rows of the 1340×26 shift map. The resultant 1340×1300 array is a map that contains a horizontal shift value for each pixel in the uncorrected spectral image. By using this map, pixels may be relocated in subsequent spectral images such as shown in FIG. 7.

Figure 5:
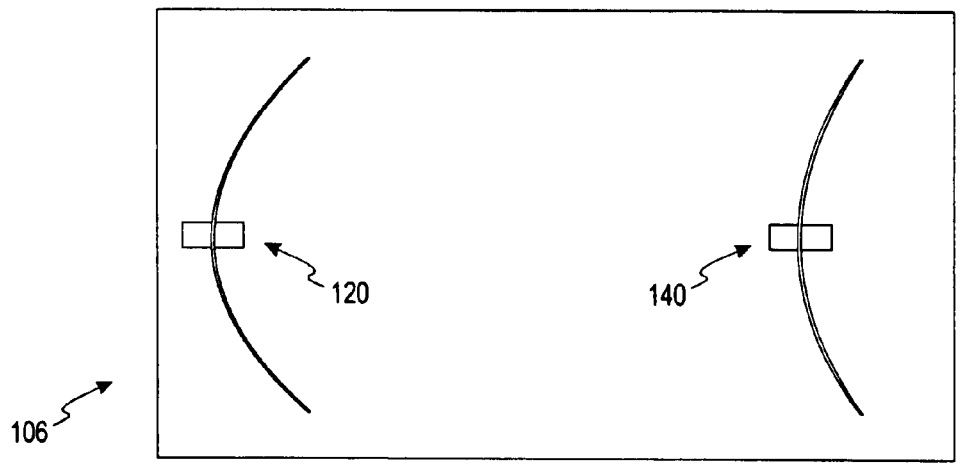
FIG. 5 depicts a subsection used in finding the apex of the curves at the far left and far right of an image according to one embodiment.
Figure 6:
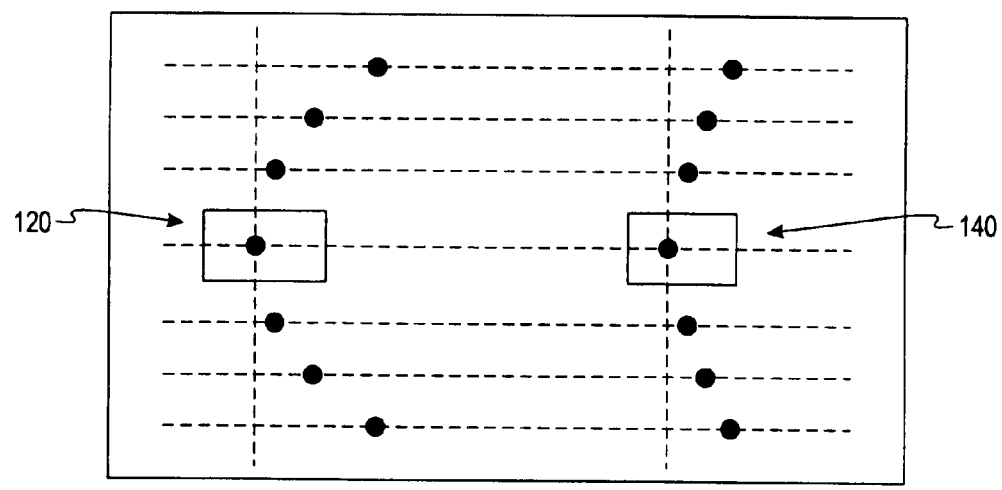
FIG. 6 depicts a series of reference points above and below the apex pixel location according to one embodiment.
Figure 7:
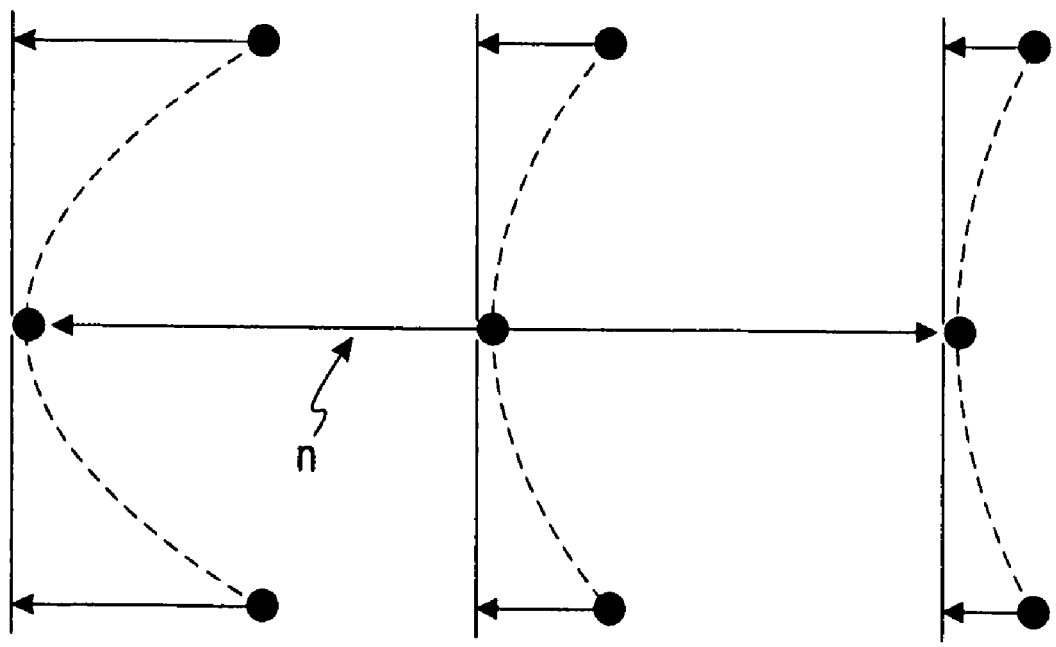
FIG. 7 depicts the difference in radiuses of curvature between the left side and right side of an image.

The above described method used with respect to FIGS. 5-7 creates a linear translation map and involves image correction in only one axis. It is contemplated that by using more model areas within the spectra, a more exact (nonlinear) map could be created depending on the type of aberration that is being corrected. In addition to correcting the image in only one axis, it is contemplated that a two dimensional correction could be performed to correct for other optical geometric distortions, such as spherical aberration, pincushion, barrel and coma.

Additionally, the method described above with respect to FIGS. 5-7 involves creating a pixel translation map to characterize a static optical system. It is contemplated, however, that if the source of the geometric distortion is changing, a geometric-correction algorithm may be applied dynamically to every image that is captured. This method may be accomplished by including a reference spectrum or geometry in each uncorrected image that is analyzed. For example, to dynamically correct a distorted spectral image, light from a known calibration source may be added with each spectral image. The algorithm would then search for and correct the image based on the location of the calibration light's spectral features.

It is contemplated that other embodiments may be used in the inventive methods. For example, a one-dimensional spatial image using incoherent fiber bundles where, on one end, the fibers are arranged as a slit. In this particular application, the software-corrected algorithm re-maps the pixels locations in the incoherent image of a "training object" to recreate the correct spatial distribution.

The software-corrected algorithm is not limited to correcting optical aberrations involving slits. For example, other size corrections of objects may be addressed in images having different but known, refractive indices. In addition to the software algorithms, hardware solutions may also be used in combination with the software-corrected algorithm to create a corrective algorithm that would be used on subsequent collected spectral images.

In addition to using Raman signals, other signals may be used to correct a spectral image for optical aberrations. In another method, a non-invasive method for determining the concentration of an analyte uses fluorescence spectral information. Analytes that may be measured using fluorescence spectral information include glucose, lipid profiles (e.g., cholesterol, triglycerides, LDL and HDL), microalbumin, hemoglobin Alc, or bilirubin. The present invention is not limited, however, to these specific analytes and it is contemplated that other analyte concentrations may be determined.

In another method, a non-invasive method uses fluorescence spectral information is used to provide a diagnosis on tissue such as skin tissue. For example, in one method, information from the collected fluorescence signals may be used to perform a general diagnosis. The general diagnosis may include identifying (a) the presence of a particular analyte; (b) a particular molecule or (c) tissue morphology. The general diagnosis can be directed to several beneficial applications. For example, potential cancerous skin lesions may be identified in one application. By identifying potential cancerous cells, the tissue removal can be minimized. In another application, the stage of cancerous cells may be identified. In a further application, the effectiveness of cancer photodynamic therapy may be tracked. It is contemplated that other diagnosis may be performed using the inventive methods.

The high-intensity light to be used with the fluorescence spectral information may be a narrow band of light, but does not necessarily have to be a narrow band of light. The high-intensity light source may come from a monochromatic light source or a polychromatic light source. It is contemplated that other light sources may be used such as a light-emitting diode (e.g., a fluorescence molecule LED), incoherent lamps, a dye laser, gas laser, ion laser, a pumped laser or light bulb.

The wavelength of the light source may vary but is generally between 300 and 10,000 nm. The fluorescence spectral information in one method may be collected in the wavelength range from about 300 nm to about 12,000 nm. It is contemplated that the fluorescence spectral information may be collected in different ranges depending on the analyte concentration to be determined.

The skin tissue or other tissue is exposed to a band of light. The tissue image may be limited to a discrete area of the skin. In another method, the tissue image may be an entire body scan. An image of the skin tissue or other tissue is optically collected. Examples of imaging optics that may be used include, but are not limited to, fiber bundles, lenses and mirrors such as discussed above with respect to FIG. 4. The image is dynamically corrected using software to optical correct for both the instrument and tissue. The corrected image is then used for diagnosis. The instrument aberrations that affect the instrument are determined. The aberrations may be related to such items as the lens and/or collections fibers. It is contemplated that the aberrations may be related to other items.

It is contemplated that the method of correcting a spectral image may be used on other items than tissue. In one method, a spectral image is corrected for optical aberrations. Raman signals from the scattered light are optically collected. The Raman signals are directed to a wavelength-separating device. The Raman signals are detected as a function of intensity and wavelength to create the spectral image. The spectral image is corrected for optical aberrations using a software algorithm to spatially reassign intensity.

In another method, a spectral image is corrected for optical aberrations using an instrument. Fluorescence signals from the scattered light are optically collected. The fluorescence signals are directed to a wavelength-separating device. The fluorescence signals are directed as a function of intensity and wavelength to create the spectral image. The spectral image is corrected for optical aberrations using a software algorithm to spatially reassign intensity.

Process A

A method for correcting a spectral image for optical aberrations, the method comprising the acts of:

exposing skin tissue to a high-intensity, narrow band of light, the narrow band of light being scattering by at least one analyte in the skin tissue;

optically collecting Raman signals from the scattered light;

directing the Raman signals to a wavelength-separating device;

detecting the Raman signals as a function of intensity and wavelength to create the spectral image; and correcting the spectral image for optical aberrations using a software algorithm to spatially reassign intensity.

Process B

The method of process A wherein the narrow band of light is a monochromatic light.

Process C

The method of process B wherein the monochromatic light is from a laser.

Process D

The method of process A wherein the narrow band of light is obtained from a polychromatic light source.

Process E

The method of process A wherein the narrow band of light has a wavelength of from about 300 to about 5,000 nm.

Process F

The method of process E wherein the narrow band of light has a wavelength of from about 800 to about 1,050 nm.

Process G

The method of process A wherein the detecting of the Raman light includes using a multi-pixel detector.

Process H

The method of process G wherein the multi-pixel detector is a charge-coupled device (CCD).

Process I

The method of process G wherein the multi-pixel detector is a diode array.

Process J

The method of process A wherein the detecting of the Raman light includes using a movable single detector.

Process K

The method of process A wherein the wavelength-separating device is a defraction element.

Process L

The method of process K wherein the defraction element is a holographic grating, diffraction grating, optical crystal or a prism.

Process M

The method of process A wherein the wavelength-separating device is a filter.

Process N

The method of process M wherein the filter is an acousto-optical tunable filter (AOTF) or a liquid crystal tunable filter (LCTF).

Process O

The method of process A wherein the optical aberrations is a curved line.

Process P
The method of process A wherein the image is a vertical straight slit image.

Process Q
The method of process A wherein the detecting of the Raman signals as a function of the intensity includes vertical binning.

Process R
A method for determining the concentration of at least one analyte in a fluid, the method comprising the acts of:
exposing skin tissue to a high-intensity, narrow band of light, the narrow band of light being scattering by at least one analyte in the skin tissue;
optically collecting the Raman signals from the scattered light;
directing the Raman signals to a wavelength-separating device;
detecting the Raman signals as a function of intensity and wavelength to create the spectral image;
correcting the spectral image for optical aberrations using a software algorithm to spatially reassign intensity; and
determining the concentration of the at least one analyte using the corrected spectral image.

Process S
The method of process R wherein the analyte is glucose.

Process T
The method of process R wherein the narrow band of light is a monochromatic light.

Process U
The method of process T wherein the monochromatic light is from a laser.

Process V
The method of process R wherein the narrow band of light is obtained from a polychromatic light source.

Process W
The method of process R wherein the narrow band of light has a wavelength of from about 300 to about 5,000 nm.

Process X
The method of process W wherein the narrow band of light has a wavelength of from about 800 to about 1,050 nm.

Process Y
The method of process R wherein the detecting of the Raman light includes using a multi-pixel detector.

Process Z
The method of process Y wherein the multi-pixel detector is a charge-coupled device (CCD).

Process AA
The method of process Y wherein the multi-pixel detector is a diode array.

Process BB
The method of process R wherein the detecting of the Raman light includes using a movable single detector.

Process CC
The method of process R wherein the wavelength-separating device is a defraction element.

Process DD
The method of process CC wherein the defraction element is a holographic grating, diffraction grating, optical crystal or a prism.

Process EE
The method of process R wherein the wavelength-separating device is a filter.

Process FF
The method of process EE wherein the filter is an acousto-optical tunable filter (AOTF) or a liquid crystal tunable filter (LCTF).

Process GG
The method of process R wherein the optical aberrations is a curved line.

Process HH
The method of process R wherein the image is a vertical straight slit image.

Process II
The method of process R wherein the detecting of the Raman signals as a function of the intensity includes vertical binning.

Process JJ
A method for correcting a spectral image for optical aberrations using an instrument, the method comprising the acts of:
exposing skin tissue to a high-intensity band of light;
optically collecting an image of the skin tissue;
dynamically correcting the image using software to optically correct for at least one of the instrument and skin tissue; and
using information from the corrected image to perform a general diagnosis.

Process KK
The method of process JJ wherein the high-intensity band of light is a monochromatic light.

Process LL
The method of process KK wherein the monochromatic light is from a laser.

Process MM
The method of process JJ wherein the high-intensity band of light is obtained from a polychromatic light source.

Process NN
The method of process JJ wherein the high-intensity band of light has a wavelength of from about 300 to about 5,000 nm.

Process OO
The method of process NN wherein the high-intensity band of light has a wavelength of from about 800 to about 1,050 nm.

Process PP
The method of process JJ wherein optically collecting an image includes using a multi-pixel detector.

Process QQ
The method of process PP wherein the multi-pixel detector is a charge-coupled device (CCD).

Process RR
The method of process PP wherein the multi-pixel detector is a diode array.

Process SS
The method of process JJ wherein the detector is a movable single detector.

Process TT
The method of process JJ wherein optically collecting an image includes using a defraction element as a wavelength-separating device.

Process UU
The method of process TT wherein the defraction element is a holographic grating, diffraction grating, optical crystal or a prism.

Process VV
The method of process JJ wherein optically collecting an image includes using a filter as a wavelength-separating device.

Process WW
The method of process VV wherein the filter is an acousto-optical tunable filter (AOTF) or a liquid crystal tunable filter (LCTF).

Process XX
A method for correcting a spectral image for optical aberrations using an instrument, the method comprising the acts of:
exposing skin tissue to a high-intensity light, the light being scattering by at least one analyte in the skin tissue;
optically collecting fluorescence signals from the scattered light;
directing the fluorescence signals to a wavelength-separating device;
detecting the fluorescence signals as a function of intensity and wavelength to create the spectral image; and
correcting the spectral image for optical aberrations using a software algorithm to spatially reassign intensity.

Process YY
The method of process XX wherein the high-intensity light is a monochromatic light.

Process ZZ
The method of process YY wherein the monochromatic light is from a laser.

Process AAA
The method of process XX wherein the high-intensity light is obtained from a polychromatic light source.

Process BBB
The method of process XX wherein the high-intensity light has a wavelength of from about 300 to about 5,000 nm.

Process CCC
The method of process XX wherein the detecting of the fluorescence light includes using a multi-pixel detector.

Process DDD
The method of process CCC wherein the multi-pixel detector is a charge-coupled device (CCD).

Process EEE
The method of process CCC wherein the multi-pixel detector is a diode array.

Process FFF
The method of process XX wherein the detecting of the fluorescence light includes using a movable single detector.

Process GGG
The method of process XX wherein the wavelength-separating device is a defraction element.

Process HHH
The method of process GGG wherein the defraction element is a holographic grating, diffraction grating, optical crystal or a prism.

Process III
The method of process XX wherein the wavelength-separating device is a filter.

Process JJJ
The method of process III wherein the filter is an acousto-optical tunable filter (AOTF) or a liquid crystal tunable filter (LCTF).

Process KKK
The method of process XX wherein the optical aberrations is a curved line.

Process LLL
The method of process XX wherein the image is a vertical straight slit image.

Process MMM
The method of process XX wherein the detecting of the Raman signals as a function of the intensity includes vertical binning.

Process NNN
A method for correcting a spectral image for optical aberrations, the method comprising the acts of:
exposing tissue to a high-intensity, narrow band of light, the narrow band of light being scattering by at least one analyte in the tissue;
optically collecting Raman signals from the scattered light;
directing the Raman signals to a wavelength-separating device;
detecting the Raman signals as a function of intensity and wavelength to create the spectral image; and
correcting the spectral image for optical aberrations using a software algorithm to spatially reassign intensity.

Process OOO
A method for determining the concentration of at least one analyte in a fluid, the method comprising the acts of:
exposing tissue to a high-intensity, narrow band of light, the narrow band of light being scattering by at least one analyte in the tissue;
optically collecting the Raman signals from the scattered light;
directing the Raman signals to a wavelength-separating device;
detecting the Raman signals as a function of intensity and wavelength to create the spectral image;
correcting the spectral image for optical aberrations using a software algorithm to spatially reassign intensity; and
determining the concentration of the at least one analyte using the corrected spectral image.

Process PPP
A method for correcting a spectral image for optical aberrations using an instrument, the method comprising the acts of:
exposing tissue to a high-intensity band of light;
optically collecting an image of the tissue;
dynamically correcting the image using software to optically correct for at least one of the instrument and the tissue; and
using information from the corrected image to perform a general diagnosis.

Process QQQ

A method for correcting a spectral image for optical aberrations using an instrument, the method comprising the acts of:
exposing tissue to a high-intensity light, the light being scattering by at least one analyte in the tissue;
optically collecting fluorescence signals from the scattered light;
directing the fluorescence signals to a wavelength-separating device;
detecting the fluorescence signals as a function of intensity and wavelength to create the spectral image; and
correcting the spectral image for optical aberrations using a software algorithm to spatially reassign intensity.

Process RRR

A method for correcting a spectral image for optical aberrations, the method comprising the acts of:
optically collecting Raman signals from the scattered light;
directing the Raman signals to a wavelength-separating device;
detecting the Raman signals as a function of intensity and wavelength to create the spectral image; and
correcting the spectral image for optical aberrations using a software algorithm to spatially reassign intensity.

Process SSS

A method for correcting a spectral image for optical aberrations using an instrument, the method comprising the acts of:
optically collecting fluorescence signals from the scattered light;
directing the fluorescence signals to a wavelength-separating device;
detecting the fluorescence signals as a function of intensity and wavelength to create the spectral image; and
correcting the spectral image for optical aberrations using a software algorithm to spatially reassign intensity.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the invention as defined by the appended claims.

What is claimed is:

1. A method for correcting a spectral image for optical aberrations, the method comprising the acts of:
exposing tissue to a high-intensity, narrow band of light, the narrow band of light being scattering by at least one analyte in the tissue;
optically collecting Raman signals from the scattered light;
directing the Raman signals to a wavelength-separating device;
detecting the Raman signals as a function of intensity and wavelength to create the spectral image; and
correcting the spectral image for optical aberrations using a software algorithm to spatially reassign intensity.

2. The method of claim 1, wherein the narrow band of light is a monochromatic light.

3. The method of claim 2, wherein the monochromatic light is from a laser.

4. The method of claim 1, wherein the narrow band of light is obtained from a polychromatic light source.

5. The method of claim 1, wherein the narrow band of light has a wavelength of from about 300 to about 5,000 nm.

6. The method of claim 5, wherein the narrow band of light has a wavelength of from about 800 to about 1,050 nm.

7. The method of claim 1, wherein the detecting of the Raman light includes using a multi-pixel detector.

8. The method of claim 1, wherein the wavelength-separating device is a defraction element.

9. The method of claim 1, wherein the wavelength-separating device is a filter.

10. A method for determining the concentration of at least one analyte in a fluid, the method comprising the acts of:
exposing skin tissue to a high-intensity, narrow band of light, the narrow band of light being scattering by at least one analyte in the tissue;
optically collecting the Raman signals from the scattered light;
directing the Raman signals to a wavelength-separating device;
detecting the Raman signals as a function of intensity and wavelength to create the spectral image;
correcting the spectral image for optical aberrations using a software algorithm to spatially reassign intensity; and
determining the concentration of the at least one analyte using the corrected spectral image.

11. The method of claim 10, wherein the analyte is glucose.

12. The method of claim 10, wherein the narrow band of light has a wavelength of from about 300 to about 5,000 nm.

13. The method of claim 12, wherein the narrow band of light has a wavelength of from about 800 to about 1,050 nm.

14. The method of claim 10, wherein the wavelength-separating device is a defraction element.

15. The method of claim 10, wherein the detecting of the Raman signals as a function of the intensity includes vertical binning.

16. A method for correcting a spectral image for optical aberrations using an instrument, the method comprising the acts of:
exposing tissue to a high-intensity light, the light being scattering by at least one analyte in the tissue;
optically collecting fluorescence signals from the scattered light;
directing the fluorescence signals to a wavelength-separating device;
detecting the fluorescence signals as a function of intensity and wavelength to create the spectral image; and
correcting the spectral image for optical aberrations using a software algorithm to spatially reassign intensity.

17. The method of claim 16, wherein the high-intensity light has a wavelength of from about 300 to about 5,000 nm.

18. A method for correcting a spectral image for optical aberrations, the method comprising the acts of:
optically collecting Raman signals from the scattered light;
directing the Raman signals to a wavelength-separating device;
detecting the Raman signals as a function of intensity and wavelength to create the spectral image; and
correcting the spectral image for optical aberrations using a software algorithm to spatially reassign intensity.

19. A method for correcting a spectral image for optical aberrations using an instrument, the method comprising the acts of:
optically collecting fluorescence signals from the scattered light;
directing the fluorescence signals to a wavelength-separating device;
detecting the fluorescence signals as a function of intensity and wavelength to create the spectral image; and
correcting the spectral image for optical aberrations using a software algorithm to spatially reassign intensity.

* * * * *